US006299842B1

United States Patent
Kozak et al.

(10) Patent No.: US 6,299,842 B1
(45) Date of Patent: Oct. 9, 2001

(54) BIOLOGICAL SAMPLING AND STORAGE CONTAINER UTILIZING A DESICCANT

(75) Inventors: Kenneth James Kozak; Ching Sui Arthur Yi, both of Cincinnati, OH (US)

(73) Assignee: Meridian Bioscience, Inc., Cincinnati, OH (US)

( * ) Notice: Subject to any disclaimer, the term of this patent is extended or adjusted under 35 U.S.C. 154(b) by 0 days.

(21) Appl. No.: 09/262,903

(22) Filed: Mar. 5, 1999

(51) Int. Cl.[7] ............................... B01L 3/00; G01N 1/00; G01N 33/48
(52) U.S. Cl. ....................... 422/102; 422/101; 435/307.1; 435/309.1; 436/177; 436/178; 604/405
(58) Field of Search ............................ 422/99–102, 61; 436/66, 176, 178, 177; 435/307.1, 309.1; 604/405–406; 206/204; 55/525, 482, 327

(56) References Cited

U.S. PATENT DOCUMENTS

| | | | |
|---|---|---|---|
| 3,421,858 | 1/1969 | Quinn | 23/253 |
| 3,640,268 | * 2/1972 | Davis . | |
| 3,732,981 | 5/1973 | Monroe | 210/94 |
| 3,819,045 | 6/1974 | Greenwald | 209/17 |
| 3,913,564 | * 10/1975 | Freshley . | |
| 3,939,044 | * 2/1976 | Wilkins et al. . | |
| 4,013,422 | * 3/1977 | Spinner et al. . | |
| 4,014,748 | * 3/1977 | Spinner et al. . | |
| 4,032,437 | 6/1977 | Greenwald | 209/17 |
| 4,066,646 | 1/1978 | LeBlanc et al. | 23/259 |
| 4,090,920 | 5/1978 | Studer | 435/288 |
| 4,148,732 | 4/1979 | Burrow et al. | 210/232 |
| 4,273,741 | 6/1981 | Levine | 422/56 |
| 4,426,295 | 1/1984 | Evans et al. | 210/772 |
| 4,453,927 | 6/1984 | Sinko | 604/52 |
| 4,492,123 | 1/1985 | Fleisher et al. | 73/864 |
| 4,578,245 | 3/1986 | Fuminori et al. | 422/56 |
| 4,615,462 | * 10/1986 | Sacherer et al. . | |
| 4,717,018 | * 1/1988 | Sacherer et al. . | |
| 4,859,610 | 8/1989 | Maggio | 436/518 |
| 4,889,256 | 12/1989 | Fowles | 220/306 |
| 5,149,506 | 9/1992 | Skiba et al. | 422/102 |
| 5,246,669 | 9/1993 | Hayashi | 422/101 |
| 5,286,454 | 2/1994 | Nilsson et al. | 422/102 |
| 5,431,884 | 7/1995 | McDonough . | |
| 5,514,341 | * 5/1996 | Urata et al. | 422/102 |
| 5,543,115 | 8/1996 | Karakawa | 422/102 |
| 5,556,544 | 9/1996 | Didier . | |
| 5,762,071 | 6/1998 | Newman et al. . | |

FOREIGN PATENT DOCUMENTS

| | | |
|---|---|---|
| 0270868 | 5/1985 | (EP) . |
| 0763477A1 | 8/1996 | (EP) . |
| WO 92/06375 | 4/1992 | (WO) . |
| 00/51496 | * 9/2000 | (WO) . |

OTHER PUBLICATIONS

Search Report—Dated Jun. 26, 2000.

* cited by examiner

Primary Examiner—Matthew O. Savage
Assistant Examiner—Marianne Ocampo
(74) Attorney, Agent, or Firm—Thompson Hine LLP

(57) ABSTRACT

The invention provides a biological sampling and storage container which is easy and sanitary to use, may be shipped through regular mail, and includes a drying material or desiccant for drying feces samples that are stored therein. The sampling and storage container consists of a body having a sampling chamber and a drying chamber which are in gaseous communication with each other. Preferably, a sampling wand is frictionally retained in the sampling chamber and the drying material is disposed in the drying chamber.

18 Claims, 2 Drawing Sheets

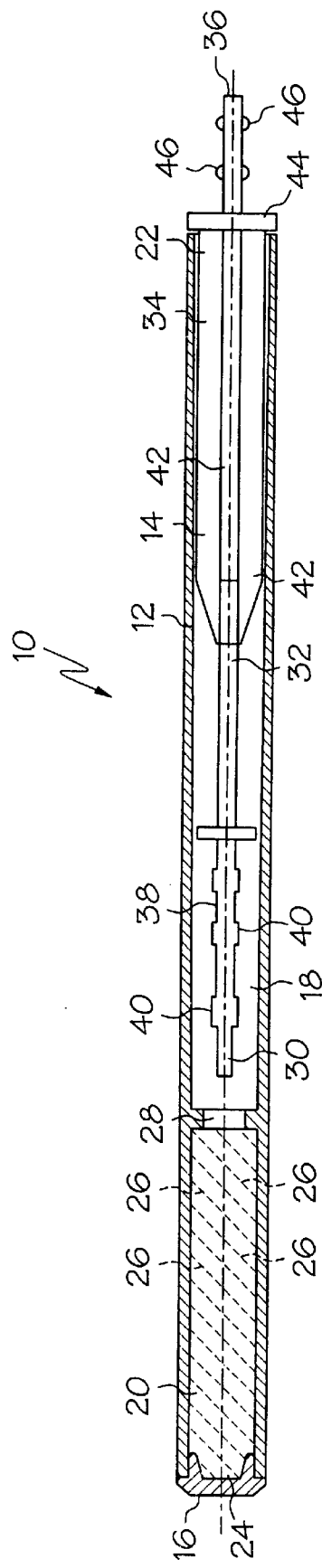
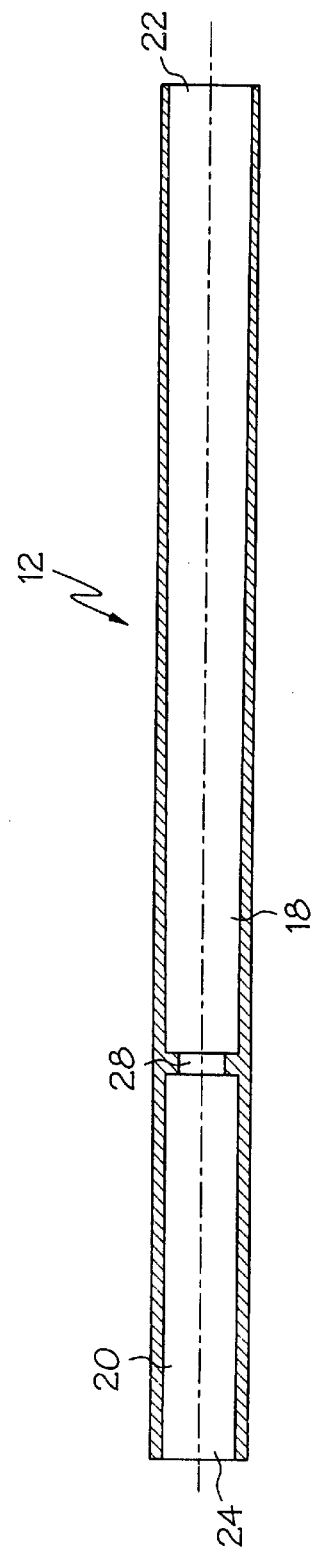

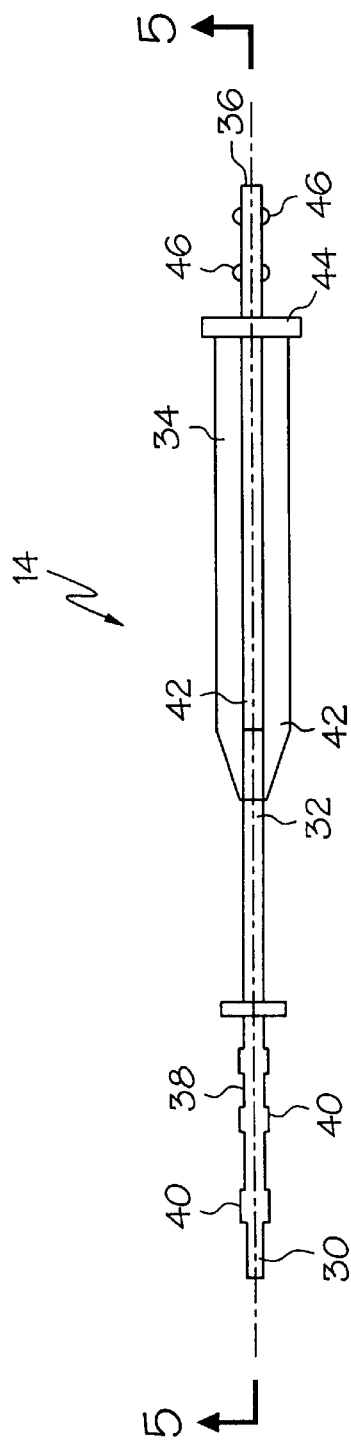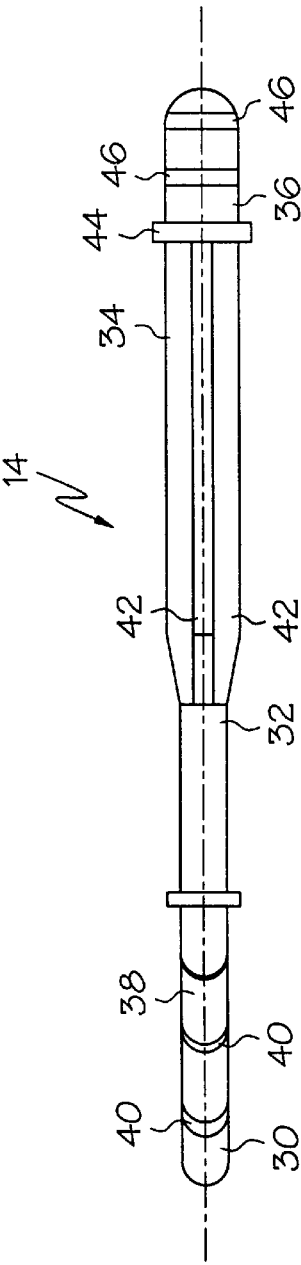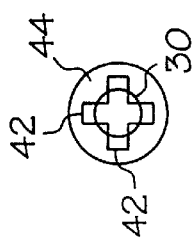

BIOLOGICAL SAMPLING AND STORAGE CONTAINER UTILIZING A DESICCANT

BACKGROUND OF THE INVENTION

This invention relates to an instrument for sampling and storing biological samples and particularly feces for use in biological or medical testing that may be easily and sanitarily packaged and sent via mail. More particularly, this invention relates to a disposable feces sampling and storage device that is inexpensive to produce and includes a desiccant to aid in drying a sample of feces that is stored therein.

In the field of medical care, lab tests that are performed on samples of body tissue, blood, urine, feces, etc., have become indispensable tools in aiding doctors with the diagnoses of the illnesses of their patients. With the continual development of new technology fueling the creation of new and improved lab equipment, new testing procedures are developed and old testing procedures are improved on an almost daily basis. While many of these tests necessarily require that blood be drawn or tissue be removed in order to perform the tests, it is generally desirable to use less invasive testing procedures whenever possible. Furthermore, some tests, such as the test for occult blood to verify the presence of gastrointestinal bleeding and tests for intestinal infections and parasites must be performed on fecal samples. Accordingly, testing procedures which use samples that can be collected using non-invasive procedures, such as urine and feces, have become increasingly popular among doctors and patients in recent years.

With the development of increased numbers of testing procedures which require the use of fecal samples, the demand for improved devices to sanitarily sample and transport these samples has correspondingly grown. In order to fill this need, there have been devices which have been designed for this purpose. For example, U.S. Pat. No. 5,149,506 to Skiba et al. discloses a stool collection and transport device which is composed of a vial having a sealable lid with an aperture formed therein for engaging a second lid. The second lid has a sampling spoon secured to the underside thereof so that a stool sample may be collected using the spoon and then sanitarily deposited in the collection vial.

While fecal sampling devices such as the one disclosed in the Skiba patent may be useful for collecting large samples which may then be sampled again using a smaller sampling device, these types of devices are generally not conducive to being sent through the mail. Furthermore, many of the latest fecal tests require that the samples collected be treated in some way shortly after collection in order to prevent degradation of the sample. For example, for some tests that are used to determine the presence of occult blood in a fecal sample, the sample must be stabilized in a liquid solution shortly after collection. This stabilization procedure is necessary to lessen the possibility that an inaccurate result is obtained from the test. Examples of sampling devices that are particularly useful for this type of test are disclosed in U.S. Pat. Nos. 5,514,341 to Urata et al. and U.S. Pat. No. 5,543,115 to Karakawa. Both of these patents disclose devices for collecting and storing fecal samples for use in testing procedures for the presence of occult blood. In order to use these devices, the sample is collected on the end of a sampling rod which is then inserted into a storage container having a fixed amount of stabilizing solution, such as glycosidase-type bacteriolytic enzyme, contained therein. Then, the container is sealed and the sample is allowed to mix with the stabilizing solution. Finally, when the sample is ready for testing, the stabilized liquid is passed through a filter which is preferably secured in the container. The testing procedure is then run on the filtrate.

While the devices disclosed in these patents are useful for testing procedures that determine the presence of occult blood and require that the sample be stabilized shortly after collection as described above, there are other testing procedures for which these types of devices are not particularly well-suited. For example, in some testing procedures, such as the occult blood assays that detect labile exoantigens and cell associated antigens of C. difficile, E. coli, it is preferred that the sample be as dry as possible. Thus, the presence of a stabilization liquid, or any liquid at all for that matter, is considered undesirable. Furthermore, since liquid is not used in the stabilization procedure, the use of a filter and dropper assembly as disclosed in the Urata patent is unnecessary.

Accordingly, it would be desirable to have a feces sampling and storage container that can be used for easily collecting and storing feces samples that need to be maintained in a relatively dry atmosphere. Preferably, the container would be small and self contained so that it would be easy and inexpensive to transport or mail and would include a device or substance for aiding in the drying of the sample, such as a desiccant. Preferably, the container would be inexpensive to produce so that it would be disposable and would be simple to use so that a patient or untrained individual could easily use the device to collect a sample with little or no instruction.

SUMMARY OF THE INVENTION

In accordance with the present invention, a feces sampling and storage container is provided which is comprised of a generally hollow body and a sampling wand shaped to frictionally or threadably engage and plug one end of the body. The sampling wand is relatively long and has a sampling tip positioned at its distal end that is designed to collect a sample of at least a minimum size when the sampling wand is inserted into a feces sample and removed. In a preferred embodiment, the sampling tip of the wand is formed in a broad tipped "spatula" shape having grooves and protrusions formed thereon. Thus, when the sampling tip is inserted into a mass of feces, an adequate amount of sample is collected in the grooves and on the tip.

Preferably, the body of the container is tubular in shape and has at least two chambers. One of the chambers, the sampling chamber, is designed to receive the sampling wand. The other chamber, the drying chamber, is designed to hold a drying device, such as a desiccant. The drying chamber is maintained in gaseous communication with the sampling chamber so that water vapor from the sample may be drawn away from the sample to the desiccant. Preferably a screen or other device, such as a constriction in the body, a wad of cotton, or a gas permeable membrane, is used to hold the desiccant in the drying chamber and away from direct contact with the sample. This is desired because direct contact between the desiccant and the sample could contaminate the sample causing inaccurate test results. Furthermore, the desiccant could become fouled thereby affecting its ability to remove water from the sample as desired.

In a preferred embodiment, the sampling wand includes a stopper end which is constructed to be frictionally received and held in a mouth of the body. The stopper seals the container preventing water vapor from getting into the container once the sample is collected while simultaneously preventing any of the sample from leaking out. This is important because the integrity of the container must be maintained during shipping and handling due to sanitary concerns. Furthermore, this prevents contamination of the sample from outside contaminants, helping to insure that the tests performed on samples retrieved and stored using the sampling and storage container of the present invention yield results which are as accurate as possible. Additionally, in a preferred embodiment, a thumb tab is formed on the top of the stopper to assist a user in the insertion and removal of the wand from the body, as well as in the sanitary collection of a sample.

Preferably the sampling and storage container of the present invention is made from a lightweight inexpensive plastic, such as polyethylene, which is liquid and gas impermeable. In a preferred construction, the container is composed of three separate pieces: the body, the sampling wand, and a plug, although other constructions are possible and considered within the scope of the invention. For example, acceptable alternate embodiments would include crimping the end of the body shut once the desiccant is placed in the drying chamber or forming the drying chamber with a closed end and inserting the desiccant from the top. Preferably, the body is molded to form a hollow tube that includes the aforementioned sampling and drying chambers. The wand, preferably formed from a relatively rigid plastic, is shaped as described above and has a stopper end with a diameter sized so that it may be frictionally fit into the sampling chamber end of the tube shaped body. A plug, having a similarly sized diameter, is also provided to close the mouth of the drying end of the tube once the desiccant has been placed in the drying chamber.

These and other objects and advantages of the present invention will be more fully understood and appreciated by reference to the following description, the accompanying drawings and the appended claims.

BRIEF DESCRIPTION OF THE DRAWINGS

FIG. 1 is a side elevational view of a feces storage and transport container utilizing a desiccant in accordance with the present invention;

FIG. 2 is a side elevational view of a body for use with the feces storage and transport container of FIG. 1;

FIG. 3 is an end view of the body of FIG. 2;

FIG. 4 is a side elevational view of a wand for use with the feces storage and transport container of FIG. 1;

FIG. 5 is a side elevational view of the wand of FIG. 4 taken along line 5—5; and FIG. 6 is an end view of the wand of FIG. 4.

DETAILED DESCRIPTION

Referring to FIG. 1, the feces sampling and transport container utilizing a desiccant of the present invention, generally designated 10, is comprised mainly of a body 12, a sampling wand 14, and a plug 16. Preferably, as shown best in FIGS. 2 and 3, the body 12 is tubular in shape and has a relatively small diameter and length (approximately ⅜ of an inch in diameter and 5 inches in length) so that it may be sent through regular mail in a standard flat envelope. The body 12 includes at least two chambers 18, 20. The sampling chamber 18 includes a mouth 22 which is shaped to frictionally receive and retain the sampling wand 14 or includes threads to threadedly receive a threaded stopper end of a sampling wand (not shown). The drying chamber 20 is positioned adjacent to and in gaseous communication with the sampling chamber 18 and also includes a mouth 24 which is shaped to receive and frictionally retain the plug 16. The drying chamber 20 is structured to hold a drying material, such as a desiccant, 26. Examples of drying materials that would be operative in the present invention include, but are not limited to, silica gels or clays, vermiculite, desiccant papers, activated alumina, zeolite compounds, calcium chloride, molecular sieves, or anhydrous chemicals such as calcium sulfate, etc. Preferably a constriction 28, cloth or screen (not shown), or gas permeable membrane (not shown), is placed between the sampling chamber 18 and the drying chamber 20 in order to keep the drying material 26 from intermixing with and contaminating or becoming fouled by the sample (not shown).

As can best be seen in FIGS. 4, 5, and 6, the sampling wand 14 is relatively long and thin and is comprised of a sampling tip 30, a shank 32, a stopper end 34, and a thumb tab 36. The sampling tip 30 is positioned at the distal end of the wand 14 and is designed to collect a sample of at least a minimum size when the sampling wand 14 is inserted into and removed from a fecal sample (not shown). In a preferred embodiment, the sampling tip 30 is formed in a broad "spatula-like" shape and has grooves 38 and protrusions 40 formed thereon. This configuration is advantageous because when the sampling tip 30 is inserted into a mass of feces (not shown), an adequate amount of sample is collected on the tip 30, as well as in between the grooves 38 and protrusions 40.

Continuing up the wand 14, a shank 32 is provided between the tip 30 and the stopper end 34. In order to increase the rigidity of the wand 14, thereby making it easier to insert into a fecal sample (not shown), the shank 32 widens into an "X" shaped branch 42 prior to joining the stopper end 34. The stopper end 34 has an effective outer diameter, formed by the legs of the "X" shaped branch 42, that is slightly larger than the inner diameter of the mouth 22 so that the wand 14 can be frictionally received and retained in the body 12. A cap 44 is formed on the wand 14 and is shaped to cover the mouth 22 thereby preventing moisture from getting into the body 12 as well as prevent sample from getting out. The thumb tab 36 is positioned above the cap 44 and includes ribs 46 positioned thereon to facilitate the removal and replacement of the wand 16 to and from the body 12.

The operation of the feces sampling and transport container utilizing a desiccant 10 of the present invention is as follows. A drying material 26 is loaded into the drying chamber 20 of the body 12 and the plug 16 is placed in the mouth 24, thereby sealing the drying material 26 therein. A user grasps the thumb tab 36 of the sampling wand 14 and urges it outward in order to remove the wand 14 from the body 12. The sampling tip 30 is then inserted into a feces sample (not shown). Preferably the wand 14 is rotated while in the sample in order to insure that an adequate amount of sample is collected on the sampling tip 30, as well as in the grooves 38. The user then reinserts the wand 16 into the mouth 22 of the body 12, being careful not to touch the sampling tip 30 to the outside of the body 12. The wand 14 is then securely seated in the body 12 until the cap 44 rests flush against the mouth 22. At this point the drying material 26 begins operating to draw moisture away from the sample (not shown) as is desired. Thus, the feces sampling and transport container 10 is in condition for shipping or transportation to a lab for testing.

While the device illustrated employs a plug 16 to seal the drying chamber 20, the tube can also be extruded with a closed end and filled with drying material from the open sampling end. The drying chamber can then be closed by inserting a cloth, screen or a ball of a material such as cotton.

While the form of the apparatus herein described constitutes a preferred embodiment of the invention, it is to be understood that the invention is not limited to this precise form of apparatus, and that changes may be made therein without departing from the scope of the invention.

What is claimed is:

1. A fecal sampling and storage container consisting essentially of:
   a tube comprised of a sampling chamber at one end of said tube and a drying chamber at the other end;
   a sampling wand coaxially retained within a mouth of said sampling chamber, said wand having a sampling tip formed on one end thereof extending into said sampling chamber;
   a gas permeable barrier positioned between said sampling chamber and said drying chamber; and
   a drying material disposed in said drying chamber.

2. A fecal sampling and storage container consisting essentially of:
   a tube comprised of a sampling chamber having a mouth and a drying chamber having a mouth;
   a sampling wand coaxially retained within said mouth of said sampling chamber, said wand having a sampling tip formed on one end thereof extending into said sampling chamber and a plug formed on the opposite end thereof for closing said sampling chamber when the wand is inserted;
   a plug shaped to be inserted into and retained in said drying chamber mouth;
   a gas permeable barrier positioned between said sampling chamber and said drying chamber; and
   a drying material in said drying chamber.

3. The container of claim 2 wherein said tube is cylindrical in shape.

4. The sampling and storage container of claim 2 wherein said drying material is silica gel.

5. The container of claim 4 wherein said drying material is silica clays.

6. The container of claim 4 wherein said drying material is molecular sieves originating from zeolite compounds which absorb molecules due to electrostatic attraction.

7. The container of claim 2 wherein said sampling tip includes a plurality of grooves formed thereon for collecting a sample within said grooves.

8. The container of claim 2 wherein said sampling tip is spatula-like in shape.

9. The container of claim 2 wherein said wand includes a cap positioned to seal said sampling chamber mouth.

10. The container of claim 2 wherein said wand is frictionally retained in said sampling chamber mouth.

11. The container of claim 2 wherein said wand is threadably retained in said sampling chamber mouth.

12. The container of claim 2 wherein said drying material is selected from the group consisting of silica gels or clays, vermiculite, zeolite compounds, calcium chloride, anhydrous chemicals, desiccant papers, activated alumina, molecular sieves, and chemical compositions having hydrophilic properties.

13. The container of claim 2 wherein said gas permeable barrier is a gas permeable membrane.

14. The container of claim 2 wherein said gas permeable barrier is a screen positioned between said sampling chamber and said drying chamber.

15. The container of claim 2 wherein said gas permeable barrier is a fine mesh cloth positioned between said sampling chamber and said drying chamber.

16. The container of claim 2 wherein said wand includes a tab positioned on an end thereof to facilitate removal of said wand from said mouth of said sampling chamber.

17. The container of claim 2 wherein said mouth of said drying chamber is mechanically closed thereby sealing said drying material in said sampling chamber.

18. The container of claim 2 where said drying material is a combination of silica gel and activated carbon.

* * * * *